United States Patent
Crenshaw et al.

(10) Patent No.: US 8,465,760 B2
(45) Date of Patent: Jun. 18, 2013

(54) METHODS OF INCREASING PRODUCTIVITY IN OLDER SOWS WHILE DECREASING FEED INTAKE

(75) Inventors: Joe David Crenshaw, Des Moines, IA (US); Joy Campbell, Ames, IA (US); Louis E. Russell, Johnston, IA (US)

(73) Assignee: APC, Inc., Ankeny, IA (US)

( * ) Notice: Subject to any disclaimer, the term of this patent is extended or adjusted under 35 U.S.C. 154(b) by 0 days.

(21) Appl. No.: 13/370,878

(22) Filed: Feb. 10, 2012

(65) Prior Publication Data

US 2012/0141593 A1   Jun. 7, 2012

Related U.S. Application Data

(62) Division of application No. 12/392,644, filed on Feb. 25, 2009, now Pat. No. 8,137,691, which is a division of application No. 11/019,951, filed on Dec. 21, 2004, now Pat. No. 7,527,805.

(51) Int. Cl.
*A23K 1/18* (2006.01)
*A23K 1/04* (2006.01)
*A23J 1/04* (2006.01)
*A23J 3/12* (2006.01)

(52) U.S. Cl.
USPC .............................................. 424/439; 426/2

(58) Field of Classification Search
None
See application file for complete search history.

(56) References Cited

U.S. PATENT DOCUMENTS

| | | | |
|---|---|---|---|
| 6,004,576 | A | 12/1999 | Weaver et al. |
| 6,534,104 | B1 | 3/2003 | DeRouchey et al. |
| 6,783,777 | B2 | 8/2004 | Miller et al. |
| 7,527,805 | B2 * | 5/2009 | Crenshaw et al. ............ 424/439 |
| 8,137,691 | B2 * | 3/2012 | Crenshaw et al. ............ 424/439 |
| 2006/0130768 | A1 | 6/2006 | Crenshaw et al. |

OTHER PUBLICATIONS

"U.S. Appl. No. 11/019,951, Final Office Action mailed Jan. 7, 2008", 11 pgs.
"U.S. Appl. No. 11/019,951, Final Office Action mailed Jan. 7, 2008", 10 pgs.
"U.S. Appl. No. 11/019,951, Non Final Office Action mailed Apr. 19, 2007", 9 pgs.
"U.S. Appl. No. 11/019,951, Response filed Oct. 18, 2007 to Non-Final Office Action mailed Apr. 19, 2007", 13 pgs.
"U.S. Appl. No. 11/019,951, Response filed Feb. 2, 2007 to Restriction Requirement mailed Oct. 7, 2006", 7 pgs.
"U.S. Appl. No. 11/019,951, Response filed Jul. 3, 2008 to Final Office Action mailed Jan. 7, 2008", 11 pgs.
"U.S. Appl. No. 11/019,951, Response filed Jul. 7, 2008 to Final Office Action mailed Jul. 7, 2008", 11 pgs.
"U.S. Appl. No. 11/019,951, Restriction Requirement mailed Oct. 7, 2006", 4 pgs.
"U.S. Appl. No. 12/392,644, Non Final Office Action mailed May 23, 2011", 9 pgs.
"U.S. Appl. No. 12/392,644, Notice of Allowance maiied Nov. 10, 2011", 5 pgs.
"U.S. Appl. No. 12/392,644, Preliminary Amendment filed Mar. 31, 2009", 3 pgs.
"U.S. Appl. No. 12/392,644, Response filed Oct. 24, 2011 to Non Final Office Action mailed May 23, 2011", 9 pgs.
Boyd, R. Dean, et al., "Segregated Parity Structure in Sow Farms to Capture Nutrition, Management and Health Opportunities", Conference Proceedings of the 13th Discover Conference on Food Animal Agriculture: Sow Productive Lifetime, Nashville, IN, (Sep. 9-12, 2007), 63-70.
Crenshaw, J. D, et al., "Lactation feed disappearance and weaning to estrus interval for sows fed spray-dried plasma.", J Anim Sci., 85(12), (Dec. 2007), 3442-53.

* cited by examiner

*Primary Examiner* — Anand Desai
*Assistant Examiner* — Melissa Mercier
(74) *Attorney, Agent, or Firm* — Schwegman Lundberg & Woessner, P.A.

(57) ABSTRACT

The present invention provides methods for feeding older sows that beneficially reduce feed intake in older sows, yet improve pig survival and weaning weight of pigs from older sows.

18 Claims, No Drawings

METHODS OF INCREASING PRODUCTIVITY IN OLDER SOWS WHILE DECREASING FEED INTAKE

CLAIM OF PRIORITY

This application is a divisional of and claims the benefit of priority under 35 U.S.C. §120 to U.S. patent application Ser. No. 12/392,644, filed on Feb. 25, 2009, entitled "METHODS OF INCREASING PRODUCTIVITY IN OLDER SOWS WHILE DECREASING FEED INTAKE," which is a divisional of and claims the benefit of priority under 35 U.S.C. §120 to U.S. patent application Ser. No. 11/019,951, filed on Dec. 21, 2004, entitled "METHODS OF INCREASING PRODUCTIVITY IN OLDER SOWS WHILE DECREASING FEED INTAKE," which issued as U.S. Pat. No. 7,527,805 on May 5, 2009, the benefit of priority of each of which is claimed hereby, and each of which are incorporated by reference herein in its entirety.

BACKGROUND OF THE INVENTION

Spray-dried plasma (SDAP) is a diverse mixture of functional components consisting of immunoglobulins, albumin, fibrinogen, lipids, growth factors, biologically active peptides (defensins, transferrin), enzymes and other factors that have biological activity within the intestine independent of their nutritional value.

In the nursery pig environment, spray-dried plasma is used extensively in feed to enhance intake, growth, and feed efficiency. Literature reviews (Coffey and Cromwell, *Pig News Info.* 22:39N-48N (2001); van Dijk et al., *Livest. Prod. Sci.* 68:263-274 (2001)) indicate an average improvement in body weight gain, feed intake, and feed efficiency of 25, 21, and 4%, respectively, due to consumption of SDAP by weanling pigs. Spray-dried plasma improves protein utilization (Jiang et al., *J. Nutr.* 130:21-26 and 2016-2019 (2000)), has anti-inflammatory effects (Touchette et al., *J. Anim. Sci.* 80:494-501 (2002); Bosi et al., *J. Anim. Sci.* 82:1764-1772 (2004): Perez-Bosque et al., *J. Nutr.* 134:2667-2672 (2004)), and reduces the severity of enteric and respiratory disease (Quigley and Drew, *Food Agric. Immunology* 12:311-318 (2000); Torrallardona et al., *J. Anim. Sci.* 81:1220-1226 (2003); Campbell et al., *J. Appl. Poult. Res.* 13:388-393 (2004)).

In lactating sows, adequate feed intake is crucial for minimizing subsequent reproductive loss. Higher daily feed intake reduces tissue loss, increases litter weight gain and reduces the probability of a prolonged wean to estrus interval (Eissen et al., *J. Anim. Sci.* 81:594-603 (2003)). Greater feed intake in lactation is also positively correlated with a greater percentage of primiparous sows expressing estrus within 8 days post-weaning (Patience et al., Swine Nutrition Guide, $2^{nd}$ Ed. Pp. 133-166 (1995)).

Inadequate feed intake by lactating sows is a problem in commercial production that is a primary factor contributing to reproductive loss and sow attrition. Additionally, older sows, or sows that have produced more than two litters of pigs, often produce fewer pigs in subsequent litters. The progeny of older sows frequently have reduced weaning weights and lower survival rates, compared to the pigs produced in prior litters.

Therefore, a need exists for methods for feeding sows that provide improved survival and weaning weight of pigs produced by older sows.

SUMMARY OF CERTAIN EMBODIMENTS OF THE INVENTION

The present invention provides a method for providing a sow with a diet that includes an amount of plasma that is effective to increase the litter weaning weight of pigs produced by a parity 3 or greater sow while reducing the feed intake of the sow.

The present invention also provides a method for feeding a parity 3 or greater sow a diet that includes an amount of plasma that is effective to increase the weaning weight of a pig produced by the parity 3 or greater sow while reducing the feed intake of the sow. The present invention further provides a method for feeding a parity 3 or greater sow a diet comprising an amount of plasma that is effective to reduce the average daily feed intake of the parity 3 or greater sow.

Additionally provided by the present invention is a method for feeding a parity 3 or greater sow with a diet that includes an amount of plasma that is effective to increase the survival rate of pigs produced by the parity 3 or greater sow while reducing the feed intake of the sow. The present invention also provides a method for feeding a parity 3 or greater sow a diet that includes an amount of plasma that is effective to improve the average daily weight gain of a pig produced by the parity 3 or greater sow while reducing the feed intake of the sow.

The present invention also provides a method for feeding a parity 3 or greater sow a diet that includes an amount of plasma that is effective to improve the survival rate of top-value pigs produced by the parity 3 or greater sow while reducing the feed intake of the sow.

Additionally provides by the present invention is a method for feeding a parity 3 or greater sow a diet that includes an amount of plasma that is effective to reduce the average daily feed intake of the parity 3 or greater sow without increasing the days to estrus interval of the sow. Further provided by the present invention is a method for feeding a parity 3 or greater sow a diet that includes an amount of plasma that is effective to reduce the average daily feed intake of the parity 3 or greater sow, wherein the days to estrus interval of the sow remains the same. Also provided by the present invention is a method for feeding a parity 3 or greater sow a diet that includes an amount of plasma that is effective to reduce the average daily feed intake of the parity 3 or greater sow and decrease the days to estrus interval of the sow.

Further, in certain embodiments of the methods of the present invention, the effective amount of plasma in the diet fed to the older sows is about 0.4-0.6% of the diet. In other embodiments of the methods of the present invention, the amount of plasma is at least 0.01% of the diet. In other embodiments of the methods of the present invention, the amount of plasma is at least 0.5% of the diet. In other embodiments of the methods of the present invention, the amount of plasma is less than 15% of the diet.

Additionally, in other embodiments of the methods of the present invention, the plasma is from a bovine, porcine, or an avian species, and may be spray-dried. In additional embodiments of the methods of the present invention, the plasma has not been separated from whole blood. In other embodiments of the methods of the present invention, the plasma has been separated from whole blood.

DETAILED DESCRIPTION OF THE INVENTION

As detailed in this application, the present invention provides methods for the use of plasma in the diets of sows. In accordance with the invention, plasma can be obtained from various sources, for example, from animal sources such as from bovine, porcine, and/or avian species. In some embodiments of the invention, the plasma is the plasma component of blood that has been separated from whole blood. In some embodiments of the invention, the plasma is plasma that has not been separated from whole blood. In certain embodiments of the invention, whole blood or plasma is combined with the feed. The plasma may be in the form of dried plasma, for example, freeze-dried, paddle-dried, and/or spray-dried animal plasma. The plasma can be dried by any method that does not cause the plasma to lose ability to promote growth when added to feed. Commercially available forms of plasma are available, for example, from APC Inc., Ankeny, Iowa.

In certain embodiments of the invention, the animal plasma is dried, e.g., is spray-dried, animal plasma, e.g., from a bovine, porcine, and/or avian species. As used herein, the term "SDAP" refers to spray-dried animal plasma from any source.

As used herein, the term "sow" refers to an adult female pig. As used herein, the phrase "lactating sow" refers to a sow that has given birth to a litter of pigs and is presently producing milk.

As used herein, the phrase "older sow" refers to a sow that has given birth to more than 2 litters of pigs. As used herein, the phrase "parity 1 sow" refers to a sow that has had its first litter of pigs. As used herein, the phrase "parity 2 sow" refers to a sow that has its second litter of pigs. As used herein, "parity 3 or greater sow" or "parity $3^+$ sow" refers to a sow that has had more than three litters of pigs.

As used herein, the term "weaning" refers to the removal of young pigs from a lactating sow. As used herein, the term "estrus" refers to a sow that is receptive to mating. As used herein, the phrase "days to estrus" refers to the number of days from weaning to estrus.

As used herein, the term "improve" may mean an increase, or that a better average is provided.

The phrase "lactation days" refers to the number of days that a sow is nursing a litter of pigs. The phrase "non-productive days," as used herein, refers to the number of days that a sow is not pregnant or lactating.

As used herein, the phrase "pigs fostered" refers to the standardization of the total number of pigs between sows during lactation within three days of birth.

The phrase "sow productivity," as used herein, is a general term that indicates overall efficiency of reproductive performance, i.e., more pigs born and weaned per litter with consistent estrus, pregnancy, and lactation cycles.

As used herein, the phrase "weanling pigs" refers to pigs that are no longer being fed by a lactating sow and have been physically removed from the lactating sow. The phrase "progeny pigs" refers to the offspring produced by a sow.

The phrase "top-value pigs," as used herein, refers to pigs that weigh 3.6 kg or heavier at a weaning age of 15 to 17 days. These pigs would be considered healthy and have a high likelihood to survive the weaning process.

The phrase "sow feed intake," as used herein, denotes the amount of feed consumed by a sow per day or per period of production.

"Pig survival to weaning," as used herein, refers to the number of pigs that survive from birth to weaning. As used herein, the phrase "litter size" refers to the number of pigs born alive within a litter of pigs. The phrase "subsequent litter size" refers to the number of pigs born alive within the next litter produced by a sow.

As used herein, the phrase "segregated parity" refers to the practice of housing sows of parity 1, 2 or older separately and in different facilities in order to reduce the spread of disease from older sows to younger sows.

The phrase "inflammatory immune response," as used herein, refers to the inflammation-causing response of the immune system to a disease, pathogen, antigen or stress.

In certain embodiments of this invention, "standard lactation feed" is a diet that is formulated and produced to be fed to lactating sows. As used herein, "standard lactation feed" provides an allowance or measure of food to sustain the daily dietary and nutritional needs of a lactating sow. For example, the National Research Council provides guidelines for the nutritional requirements of lactating sows. (See National Research Council, Nutrient Requirements of Swine, Tenth Revised Ed., 1998; tables 10-9, 10-10 and 10-11, p. 119-121; National Academy Press, Washington D.C., U.S.A.).

According to the invention, Applicants have unexpectedly discovered that plasma, when fed to older sows, was effective to lower the daily feed intake of the older sows, while improving progeny pig survival to weaning. Additionally, Applicants have unexpectedly discovered that the number of top-value pigs and the survival rate of top-value pigs improved when older sows were fed plasma, while the feed intake of the older sows was reduced. It has also been unexpectedly discovered that when plasma is included in the feed of older sows, progeny pig survival, number of progeny pigs weaned, litter weaning weight, average pig weaning weight, and average daily weight gain of progeny pigs from older sows are improved with no change in days to estrus interval. It has further been unexpectedly discovered that when plasma is fed to an older sow, the average daily feed intake of the older sow is reduced without increasing the days to estrus interval. It has also been unexpectedly discovered that when plasma is fed to an older sow, the average daily feed intake of the older sow is reduced and the days to estrus interval of the sow remains the same. It has further been unexpectedly discovered that when plasma is fed to an older sow, the average daily feed intake of the older sow is reduced and the days to estrus interval of the sow decreases. Again, these results are unexpected, since older sows fed plasma consumed less feed per day. Thus in one embodiment of the invention, the plasma provided to the older sows is in an amount that reduces the average daily feed intake of the older sows.

In some embodiments of the invention, the plasma provided to the older sows is provided in an amount that increases the average daily weight gain (ADG) of the progeny pigs, while reducing the feed intake of the older sows. In other embodiments of the invention, the plasma provided to the older sows is provided in an amount that increases the average daily feed intake (ADFI) of the progeny pigs, while reducing the feed intake of the older sows. In further embodiments of the invention, the plasma provided to the older sows is provided in an amount that increases the weaning weight (WW) of the progeny pigs, while reducing the feed intake of the older sows. In an alternate embodiment of the invention, the plasma provided to the older sows is provided in an amount that increases the litter weaning weight of pigs produced by older sows while reducing the feed intake of the older sows. In additional embodiments of the invention, the plasma provided to the older sows is provided in an amount that improves the survival to rate of the pigs produced by the sows while reducing the feed intake of the sows.

Additionally, according to the invention, Applicants have unexpectedly discovered that SDAP, when fed to older sows, was effective to lower the daily feed intake of the older sows, while improving progeny pig survival to weaning. Additionally, Applicants have unexpectedly discovered that the number of top-value pigs and the survival rate of top-value pigs improved when older sows were fed SDAP, while the feed intake of the older sows was reduced. It has also been unexpectedly discovered that when SDAP is included in the feed of older sows, progeny pig survival, number of progeny pigs weaned, litter weaning weight, average pig weaning weight, and average daily weight gain of progeny pigs from older sows are improved with no change in the days to estrus interval. It has further been unexpectedly discovered that when SDAP is fed to an older sow, the average daily feed intake of the older sow is reduced without increasing the days to estrus interval. It has also been unexpectedly discovered that when SDAP is fed to an older sow, the average daily feed intake of the older sow is reduced and the days to estrus interval of the sow remains the same. It has further been unexpectedly discovered that when SDAP is fed to an older sow, the average daily feed intake of the older sow is reduced and the days to estrus interval of the sow decreases. Again, these results are unexpected, since older sows fed SDAP consumed less feed per day. Thus in one embodiment of the invention, the SDAP provided to the older sows is in an amount that reduces the average daily feed intake of the older sows.

In some embodiments of the invention, the SDAP provided to the older sows is provided in an amount that increases the average daily weight gain (ADG) of the progeny pigs, while reducing the feed intake of the older sows. In other embodiments of the invention, the SDAP provided to the older sows is provided in an amount that increases the average daily feed intake (ADFI) of the progeny pigs, while reducing the feed intake of the older sows. In further embodiments of the invention, the SDAP provided to the older sows is provided in an amount that increases the weaning weight (WW) of the progeny pigs, while reducing the feed intake of the older sows. In an alternate embodiment of the invention, the SDAP provided to the older sows is provided in an amount that increases the litter weaning weight of pigs produced by older sows while reducing the feed intake of the older sows. In additional embodiments of the invention, the SDAP provided to the older sows is provided in an amount that improves the survival to rate of the pigs produced by the sows while reducing the feed intake of the sows.

Specific embodiments and values listed below are for illustration only; they do not exclude other defined values or other values within defined ranges.

In one specific embodiment of the present invention, the amount of plasma fed to the sows is at least about 0.01% of the diet. In another specific embodiment of the present invention, the amount of plasma fed to the sows is at least about 0.05% of the diet; in another specific embodiment of the present invention, the amount of plasma fed to the sows is at least about 0.1% of the diet; in another specific embodiment of the present invention, the amount of plasma fed to the sows is at least about 0.2% of the diet; in another specific embodiment of the present invention, the amount of plasma fed to the sows is at least about 0.3% of the diet; in another specific embodiment of the present invention, the amount of plasma fed to the sows is at least about 0.4% of the diet; in another specific embodiment of the present invention, the amount of plasma fed to the sows is at least about 0.5% of the diet.

In another specific embodiment of the present invention, the amount of plasma fed to the sows is less than about 15% of the diet; in another specific embodiment of the invention, the amount of plasma fed to the sows is less than about 0.12% of the diet; in another specific embodiment of the invention, the amount of plasma fed to the sows is less than about 10% of the diet; in another specific embodiment of the invention, the amount of plasma fed to the sows is less than about 8% of the diet; in another specific embodiment of the invention, the amount of plasma fed to the sows is less than about 5% of the diet; in another specific embodiment of the invention, the amount of plasma fed to the sows is less than about 3% of the diet; in another specific embodiment of the invention, the amount of plasma fed to the sows is less than about 1% of the diet; in another specific embodiment of the invention, the amount of plasma fed to the sows is less than about 0.6% of the diet.

In certain embodiments of the invention, the amount of plasma fed to the sows is about 0.01-15% of the diet. In other embodiments of the present invention, the amount of plasma is about 0.05-10% of the diet. In further embodiments of the invention, the amount of plasma is about 0.1-5% of the diet. In other embodiments of the invention, the amount of plasma is about 0.3-2% of the diet. In further embodiments of the invention, the amount of plasma is about 0.4-0.6% of the diet.

The percentage of the plasma fed to the sows may, of course, be varied and may conveniently be between about 0.01-15% of the diet. The amount of plasma fed to the sows is such that an effective amount will be provided.

In one specific embodiment of the present invention, the amount of SDAP fed to the sows is at least about 0.01% of the diet. In another specific embodiment of the present invention, the amount of SDAP fed to the sows is at least about 0.05% of the diet; in another specific embodiment of the present invention, the amount of SDAP fed to the sows is at least about 0.1% of the diet; in another specific embodiment of the present invention, the amount of SDAP fed to the sows is at least about 0.2% of the diet; in another specific embodiment of the present invention, the amount of SDAP fed to the sows is at least about 0.3% of the diet; in another specific embodiment of the present invention, the amount of SDAP fed to the sows is at least about 0.4% of the diet; in another specific embodiment of the present invention, the amount of SDAP fed to the sows is at least about 0.5% of the diet.

In another specific embodiment of the present invention, the amount of SDAP fed to the sows is less than about 15% of the diet; in another specific embodiment of the invention, the amount of SDAP fed to the sows is less than about 0.12% of the diet; in another specific embodiment of the invention, the amount of SDAP fed to the sows is less than about 10% of the diet; in another specific embodiment of the invention, the amount of SDAP fed to the sows is less than about 8% of the diet; in another specific embodiment of the invention, the amount of SDAP fed to the sows is less than about 5% of the diet; in another specific embodiment of the invention, the amount of SDAP fed to the sows is less than about 3% of the diet; in another specific embodiment of the invention, the amount of SDAP fed to the sows is less than about 1% of the diet; in another specific embodiment of the invention, the amount of SDAP fed to the sows is less than about 0.6% of the diet.

In further embodiments of the present invention, SDAP is fed to the sows. In those embodiments of the invention, the amount of SDAP fed to the sows is preferably about 0.01-15% of the diet. In certain embodiments of the present invention, the amount of SDAP is preferably about 0.05-10% of the diet. In further embodiments of the invention, the amount of SDAP is more preferably about 0.1-5% of the diet. More preferably, in certain embodiments of the invention, the amount of SDAP is about 0.3-2% of the diet. Most preferably, the amount of SDAP is about 0.4-0.6%) of the diet.

The percentage of the SDAP fed to the sows may, of course, be varied and may conveniently be between about 0.01-15% of the diet. The amount of SDAP fed to the sows is such that an effective amount will be provided.

The invention will now be illustrated by the following non-limiting Examples.

EXAMPLES

Example I

Effect of Spray-Dried Plasma in Lactation Feed in a Segregated-Parity Sow Herd Introduction:

Spray-dried animal plasma (SDAP) increases feed intake in weanling pigs and is thought to reduce inflammatory immune response, particularly at the intestinal mucosa. Heat stress reduces voluntary feed intake in sows resulting in maternal weight loss and increased days to breeding. The objectives of this study were to evaluate the effects of SDAP (Appetein™, APC, Ankeny, Iowa, U.S.A.) in lactation feed on sow feed intake, pig survival to weaning, days to estrus, and subsequent litter size in a segregated-parity commercial sow herd.

Dietary Treatments:

Lactation feed treatments were pelleted and contained either 0 or 0.5% dietary SDAP (Appetein™). Three control formulations (one for each parity group) were used, consisting of the standard lactation feed for each parity group. See Table 1 for dietary treatments. Control, P1, P2, and P3+ sows were fed diets formulated to contain 3.3 Mcal ME/kg (ME=metabolizable energy) and 1.30%, 1.04% and 1.04% total lysine for the respective parity groups. Major ingredients included corn, sorghum grain, soybean meal, wheat midds, bakery by-products, and choice white grease or tallow. No other animal proteins, metabolic modifiers or antimicrobials were included in the dietary treatments. Supplemental chromium picolinate was included in all diets at 0.05%.

TABLE 1

Dietary treatments fed during Experiment I

| Ingredient | SDAP Diet % | P3 Diet % | P2 Diet % | P1 Diet % |
|---|---|---|---|---|
| Milo | 35.27 | 22.92 | 35.81 | 24.39 |
| Corn 8.5 | 15.00 | 9.70 | 15.00 | 0.00 |
| Soy Meal 47.5 | 19.60 | 19.71 | 19.85 | 29.90 |
| Wheat Midds | 20.00 | 18.32 | 20.00 | 17.86 |
| Bakery ARK | 0.00 | 23.34 | 0.00 | 20.00 |
| Choice white grease | 3.70 | 1.75 | 3.35 | 2.00 |
| CWG (Spray-On) | 2.00 | 0.80 | 2.00 | 2.05 |
| Limestone | 1.25 | 1.25 | 1.25 | 1.32 |
| Monocal 21P 18C | 0.90 | 0.71 | 0.90 | 1.03 |
| Dynamate K—Mg | 0.75 | 0.75 | 0.75 | 0.75 |
| Plasma | 0.50 | 0.00 | 0.00 | 0.00 |
| Salt | 0.35 | 0.00 | 0.35 | 0.05 |
| L-lysine | 0.20 | 0.23 | 0.23 | 0.17 |
| Nursery VTM | 0.00 | 0.18 | 0.00 | 0.00 |
| Sow VTM | 0.15 | 0.00 | 0.15 | 0.15 |
| Choline 60 Dry | 0.13 | 0.13 | 0.13 | 0.13 |
| Chromax | 0.05 | 0.06 | 0.05 | 0.05 |
| Zinc Oxide | 0.10 | 0.10 | 0.10 | 0.10 |
| Threonine | 0.05 | 0.06 | 0.07 | 0.06 |
| dL-Methionine | 0.00 | 0.00 | 0.01 | 0.00 |
| Total | 100.00 | 100.00 | 100.00 | 100.00 |
| Swine ME, kcal/lb | 1519 | 1501 | 1508 | 1507 |
| Lysine, % | 1.04 | 1.06 | 1.04 | 1.30 |

Animals and Facilities:

The study was carried out at a commercial farm that practices segregated parity management and involved 894 PIC sows. Parity 1 (P1) and parity 2 (P2) sows were housed at separate sites and parity 3 and older sows (P3+) were housed at two other separate sites. Each site had 16 farrowing rooms with 28 crates per room. There were 4, 4 and 8 rooms assigned per treatment by parity 1, 2 and 3+ sows that provided 112, 112 and 223 sows per treatment by parity group, respectively. Sows farrowed during August and September when heat stress would be expected to reduce feed intake. Since one feed bin supplied feed to 2 farrowing rooms, treatment was assigned to feed bins. An automated feed system delivered 4 feedings per day. Daily feed intake was recorded on individual sow feed record cards. Diets were fed from the day the sows entered the farrowing room until weaning. Creep feed was not offered to pigs. Supplemental milk replacer (containing SDAP) was not provided to pigs in this experiment. Data collected included individual lactation feed intake, lactation days, pigs fostered and weaned per litter, pig survival to weaning, days to estrus, and number of pigs born alive during the next litter.

Results:

Treatment effects by parity are presented in Table 2. Lactation length averaged 18.4 days across all parities, but was longer for P1 sows fed SDAP, and less for P3+ sows fed SDAP (See Table 2.) The number of pigs per litter after fostering was less ($P<0.05$) for P3+ sows fed SDAP. Both P1 and P2 sows fed SDAP had greater ($P<0.0001$) daily feed intake (+0.5 kg/d). Conversely, P3+ sows fed SDAP had less ($P<0.01$) daily feed intake (−0.3 kg/d), but pig survival to weaning was improved ($P<0.05$) (89.3 vs 92.0%) for P3+ sows. Lactation length was used as a covariable in statistical analysis of the feed intake data for each parity group, yet treatment effect on feed intake remained highly significant ($P<0.04$) for all parity groups.

Parity 1 sows fed SDAP (Table 2) had reduced days to estrus (−2.5 d) and a greater percentage of P1 sows expressed estrus by day 7 postweaning ($P<0.01$) (60.2 vs 82.2%). The reduced days to estrus treatment effect was further evaluated by covariable analysis, Neither lactation length, pigs fostered per litter, or average daily feed intake, when used as a covariable, altered the significance of the treatment effect of SDAP on days to estrus in P1 sows. Although P3 sows had reduced ($P<0.05$) average daily feed intake, the number of days to estrus or percentage in estrus by day 7 was unchanged ($P>0.10$).

TABLE 2

Impact of SDAP in Lactation Feed in Segregated-Parity Sows

| Variable [a] | Parity | SDAP 0.0% | SDAP 0.5% | Trt effect (P) |
|---|---|---|---|---|
| Lactation days | P1 | 17.7 | 19.2 | <0.0001 |
|  | P2 | 18.1 | 18.4 | 0.12 |
|  | P3+ | 18.7 | 18.2 | <0.0001 |
| Pigs fostered | P1 | 10.70 | 10.58 | 0.16 |
|  | P2 | 10.78 | 10.63 | 0.16 |
|  | P3+ | 11.20 | 10.78 | <0.0001 |
| Pigs weaned | P1 | 9.88 | 9.90 | 0.93 |
|  | P2 | 9.54 | 9.55 | 0.93 |
|  | P3+ | 9.98 | 9.89 | 0.52 |
| Pig survival, % | P1 | 92.5 | 93.8 | 0.39 |
|  | P2 | 88.7 | 90.1 | 0.43 |
|  | P3+ | 89.3 | 92.0 | 0.0260 |
| ADFI, kg/d | P1 | 4.3 | 4.8 | <0.0001 |
|  | P2 | 5.0 | 5.5 | <0.0001 |
|  | P3+ | 5.8 | 5.5 | 0.0094 |
| Days to estrus | P1 | 8.3 | 5.7 | 0.0002 |
|  | P2 | 6.1 | 6.6 | 0.49 |
|  | P3+ | 6.5 | 6.3 | 0.81 |
| Non-productive days [b] | P1 | 12.3 | 9.8 | 0.07 |
|  | P2 | 9.4 | 10.6 | 0.29 |
|  | P3+ | 10.3 | 10.0 | 0.79 |

TABLE 2-continued

Impact of SDAP in Lactation Feed in Segregated-Parity Sows

| | | SDAP | | |
| Variable [a] | Parity | 0.0% | 0.5% | Trt effect (P) |
|---|---|---|---|---|
| % in estrus D 7 [c] | P1 | 60.2 | 82.2 | 0.0004 |
| | P2 | 80.4 | 82.2 | 0.73 |
| | P3+ | 80.6 | 79.0 | 0.69 |

[a] Average lactation length = 18.4 d. Sows/trt/parity = 112, 112, 223.
[b] Days from weaning to next litter—114 gestation days.
[c] Values are least square means using Chi-square analysis.

Conclusions:

Spray dried animal plasma (0.5%) increased daily feed intake in P1 and P2 sows and reduced days to estrus and percentage in estrus by day 7 in P1 sows. In older sows (P3+) fed SDAP, pig survival improved, while daily feed intake decreased. Additionally, in older sows (P3+) fed SDAP, there was no change in the number of days to estrus or the percentage in estrus by day 7.

Example II

Effect of Spray-Dried Plasma in Lactation Feed in an Older Sow Herd

Introduction:

Due to the lower feed intake and improved pig survival results of P3+ sows fed SDAP in Example 1, it was decided to repeat the experiment using similar dietary modification (0 vs 0.5% SDAP) in diets for older sows (P3+). The goal of this experiment was to obtain additional feed intake information, pig survival data, litter weights and number of top-value pigs (>3.6 kg) weaned.

Dietary Treatments:

Lactation feed treatments were pelleted and contained either 0 or 0.5% dietary SDAP (Appetein™ APC, Ankeny, Iowa, U.S.A.) and both control and SDAP diets were formulated to contain 3.3 Mcal ME/kg and 1.00% total lysine. Major ingredients included corn, soybean meal, wheat midds and animal-vegetable fat blend. No other animal proteins, metabolic modifiers or antimicrobials were included in the dietary treatments. Supplemental chromium picolinate was included in all diets at 0.10%. See Table 3 for dietary treatments.

Daily feed intake was recorded on individual sow feed record cards. Diets were fed from the day sows entered the farrowing room until weaning. Creep feed was not offered to pigs. Supplemental milk replacer (containing SDAP) was provided to all pigs during day 1-12 of lactation in this experiment.

TABLE 3

Dietary treatments fed to older sows

| Ingredient | Control % | SDAP Diet % |
|---|---|---|
| Milo (Low Tannin) | 30.00 | 30.00 |
| Corn | 22.17 | 28.00 |
| Soybean Meal 47 | 19.92 | 19.35 |
| Wheat Midds | 13.79 | 10.31 |
| Bakery ARK | 7.42 | 5.07 |
| Fat, A-V Blend | 3.00 | 3.00 |
| Limestone | 1.25 | 1.26 |
| Monocal 21P 18Ca | 0.82 | 0.85 |
| Dynamate K—Mg | 0.65 | 0.65 |

TABLE 3-continued

Dietary treatments fed to older sows

| Ingredient | Control % | SDAP Diet % |
|---|---|---|
| Plasma | 0.00 | 0.50 |
| Salt | 0.25 | 0.28 |
| L-lysine | 0.20 | 0.20 |
| VTM | 0.19 | 0.19 |
| Choline 60 Dry | 0.17 | 0.17 |
| Chromax 0.04% | 0.10 | 0.10 |
| L-Threonine | 0.07 | 0.07 |
| dL-Methionine | 0.02 | 0.01 |
| Total | 100.00 | 100.00 |
| Swine ME, kcal/lb | 1492 | 1500 |
| Lysine, % | 1.00 | 1.00 |

Animals and Facilities:

The study was conducted at a commercial farm that practices segregated parity management and involved 588 P3+ PIC sows. Each site had 16 farrowing rooms with 28 crates per room. Sows farrowed during August and September when heat stress would be expected to reduce feed intake. Since one feed bin supplied feed to 2 farrowing rooms, treatment was assigned to feed bins. An automated feed system delivered 4 feedings per day. Daily feed delivered was recorded on individual sow feed record cards. Diets were fed from the day the sows entered the farrowing room until weaning. Creep feed was not offered to pigs. Data collected included individual lactation feed intake, lactation days, pigs fostered and weaned per litter, pig survival to weaning, and days to estrus.

Results:

Average lactation length was 16.9 days and was not different between treatments, nor was pigs fostered per litter different between treatments (See Table 4). A very similar response to SDAP for ADFI occurred in this experiment as observed in Example 1. Average daily feed intake was reduced (P=0.0016) for P3+ sows fed SDAP (−0.3 kg/d).

In this Example, litters were weighed one day before weaning and the number of top-value pigs per litter (pigs that weighed>3.6 kg) was recorded. Survival of all pigs per litter was not affected by treatment (P=0.4203). However, survival of top-value pigs was improved (P=0.10) for sows fed SDAP. The number of top-value pigs weaned (+0.3 pigs) was also improved (P<0.03) for sows fed SDAP. Litter weaning weight, average pig weaning weight and average daily gain of pigs from sows fed SDAP was improved (P<0.01) suggesting improved milk production by sows fed SDAP. These results are unexpected, since sows fed SDAP consumed less feed per day and pigs from sows fed either treatment had access to supplemental milk replacer during day 1 to 12 of lactation.

TABLE 4

Impact of SDAP in Lactation Feed in Older Sows

| | SDAP | | |
| Variable [a] | 0.0% | 0.5% | Trt effect (P) |
|---|---|---|---|
| Sow ADFI, kg/d | 5.3 | 5.0 | 0.0016 |
| Pigs fostered/litter | 10.7 | 10.8 | 0.3309 |
| Pigs weaned/litter | 9.67 | 9.82 | 0.2221 |
| Survival all pigs, % | 90.5 | 91.4 | 0.4203 |
| Top-value pigs weaned [b] | 8.93 | 9.24 | 0.0286 |
| Survival top-value pigs | 83.8 | 86.0 | 0.1002 |
| Litter wean weight all pigs, kg | 50.7 | 54.1 | 0.0004 |

TABLE 4-continued

Impact of SDAP in Lactation Feed in Older Sows

| Variable[a] | SDAP | | Trt effect (P) |
|---|---|---|---|
| | 0.0% | 0.5% | |
| Avg. pig wean wt., kg [c] | 5.24 | 5.50 | 0.0003 |
| ADG, g/d [d] | 240 | 255 | 0.0001 |

[a] Avg. lactation length = 16.9 d. Avg. parity = 5.95. Litters = 280 and 308 for 0 and 0.5% SDAP.
[b] Top-value pigs weighed >3.6 kg
[c] Sows = 268 and 284 for 0 and 0.5% SDAP.
[d] Calculated from farm historical birth weight data (avg. = 1.43 kg).

All publications, patents and patent documents are incorporated by reference herein, as though individually incorporated by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

We claim:

1. A method to increase the survival rate of pigs produced by a parity 3 or greater sow while reducing the feed intake of the parity 3 or greater sow, comprising providing the parity 3 or greater sow a diet comprising an effective amount of plasma so that the survival rate of pigs produced by the sow is increased while the feed intake of the sow is reduced.

2. The method of claim 1, wherein the amount of plasma is about 0.4-0.6% of the diet.

3. The method of claim 1, wherein the amount of plasma is at least about 0.01% of the diet.

4. The method of claim 1, wherein the amount of plasma is at least about 0.5% of the diet.

5. The method of claim 1, wherein the amount of plasma is less than about 15% of the diet.

6. The method of claim 1, wherein the plasma is from a bovine, porcine, or avian species.

7. The method of claim 1, wherein the plasma is spray-dried.

8. The method of claim 1, wherein the plasma has not been separated from whole blood.

9. The method of claim 1, wherein the plasma has been separated from whole blood.

10. A method to improve the survival rate of top-value pigs produced by a parity 3 or greater sow while reducing the feed intake of the parity 3 or greater sow, comprising providing the parity 3 or greater sow a diet comprising an effective amount of plasma so that the survival rate of top-value pigs produced by the sow is improved while the feed intake of the sow is reduced.

11. The method of claim 10, wherein the amount of plasma is about 0.4-0.6% of the diet.

12. The method of claim 10, wherein the amount of plasma is at least about 0.01% of the diet.

13. The method of claim 10, wherein the amount of plasma is at least about 0.5% of the diet.

14. The method of claim 10, wherein the amount of plasma is less than about 15% of the diet.

15. The method of claim 10, wherein the plasma is from a bovine, porcine, or avian species.

16. The method of claim 10, wherein the plasma is spray-dried.

17. The method of claim 10, wherein the plasma has not been separated from whole blood.

18. The method of claim 10, wherein the plasma has been separated from whole blood.

* * * * *